(12) United States Patent
Kanno

(10) Patent No.: US 7,601,344 B2
(45) Date of Patent: Oct. 13, 2009

(54) HOST CELLS OBTAINED BY INTRODUCING AND EXPRESSING VHL GENE IN CANCER CELLS OR EMBRYONIC STEM CELLS

(75) Inventor: Hiroshi Kanno, Kanagawa (JP)

(73) Assignee: Cell Free Sciences Co., Ltd., Tokyo (JP)

( * ) Notice: Subject to any disclaimer, the term of this patent is extended or adjusted under 35 U.S.C. 154(b) by 315 days.

(21) Appl. No.: 11/640,905

(22) Filed: Dec. 19, 2006

(65) Prior Publication Data

US 2007/0116692 A1 May 24, 2007

Related U.S. Application Data

(62) Division of application No. 10/381,488, filed as application No. PCT/JP00/06668 on Sep. 27, 2000, now abandoned.

(51) Int. Cl.
*A01N 63/00* (2006.01)
*C07H 21/02* (2006.01)
*C07H 21/04* (2006.01)
*C12Q 1/70* (2006.01)

(52) U.S. Cl. ............. 424/93.21; 536/23.1; 435/5
(58) Field of Classification Search .............. None
See application file for complete search history.

(56) References Cited

U.S. PATENT DOCUMENTS 5,851,814 A * 12/1998 Green et al. ............. 435/218

FOREIGN PATENT DOCUMENTS

WO 00/69908 11/2000

OTHER PUBLICATIONS

Kanno et al., 2000, Cancer Research, 60: 2820-2824.*
Isacson et al., *Nature Medicine*, vol. 3, pp. 964-969, 1997.
Rothstein et al., *Nature Biotechnology*, vol. 22, pp. 283-285, 2004.
Long et al., *Stem Cells and Development*, vol. 14, 65-69. 2005.
Liu et al., *Journal of Cellular Biochemistry*, vol. 88, pp. 29-40, 2003.
Correia et al. *Annals of Medicine*, vol. 37, pp. 487-498, 2005.
Hammer et al., *J. of Anim. Sci.*, vol. 63, pp. 269-278, 1986.
Traut, *Molecular and Cellular Biology*, vol. 30, pp. 3-10, 1986.
Collins et al., *Molecular and Cellular Biology*, vol. 21, pp. 3609-3615, 2001.
H. Kanno et al., "Role of the von Hippel-Lindau Tumor Suppressor Protein during Neuronal Differentiation", Cancer Research , vol. 60, Jun. 2000, pp. 2820-2824.
F. Latif et al., "Identification of the von Hippel-Lindau Disease Tumor Suppressor Gene", Science, vol. 260, May 1993, pp. 1317-1320.
J. Gnarra et al., "Molecular Cloning of the von Hippel-Lindau Tumor Suppressor Gene and Its Role in Renal Carcinoma", Biochemical et Biophysica Acta, vol. 1242, No. 3, Mar. 1996, pp. 201-210.
D. Watkins et al., "Genetics Prognosis and Therapy of Central Nervous System Tumors", Cancer Detection and Prevention, vol. 18, No. 2, 1994, pp. 139-144.
J. McDonald et al., "Transplanted Embryonic Stem Cells Survive, Differentiate and Promote Recovery in Injured Rat Spinal Cord", Nature Medicine, vol. 5, No. 12, Dec. 1999, pp. 1410-1412.
Kanno et al., "Role of the von Hippel-Lindau Tumor Suppressor Protein during Neuronal Differentiation", *Cancer Research*, vol. 60, pp. 2820-2824, 2000.
Kanno et al., "Regulation of Differentiation by VHL Gene in Neural Stem Cells and Cell Death", *Neuroimmunological Research*, vol. 13, pp. 85-90, 2003 (including English Abstract).
Ohh et al., "Synthetic peptides define critical contacts between elongin C, elongin B, and the von Hippel-Lindau protein", *The Journal of Clinical Investigation*, vol. 104, No. 11, pp. 1583-1591, 1999.
Asao, "Elongin BC complex that controls multiple intracellular functions", *Biochemistry*, vol. 71, No. 4, pp. 278-283, 1999 in Japanese with English translation.
Tanaka, "The role of von Hippel-Lindau protein in the differentiation of neural progenitor cells under normoxic and anoxic conditions", *Neuroscience Letters*, vol. 383, pp. 28-32, 2005.
Yamada et al., "Transfer of the von Hippel-Lindau Gene to Neuronal Progenitor Cells in Treatment for Parkinson's Disease", *Ann. Neurol.*, vol. 54, pp. 352-359, 2003.
Kim and Morshead, *J. of Neurosci.*, vol. 23, pp. 10703-10709, 2003.
Fisher, *Neurobiology of Disease*, vol. 4, pp. 1-22, 1997.
Murray et al., "Transgenic Animals in Agriculture", CAB International: Oxon, pp. 59-60, 1999.
Murata et al., *Cancer Research*, vol. 62, pp. 7004-7011, 2002.

* cited by examiner

*Primary Examiner*—Joanne Hama
(74) *Attorney, Agent, or Firm*—Wenderoth, Lind & Ponack, L.L.P.

(57) ABSTRACT

The present invention relates to host cells that can function as neurons which are obtained by introducing and expressing von Hippel-Lindau gene in cancer cells, such as neuroblastoma cells and anaplastic oncocytes derived from the nerve system, or embryonic stem cells. The obtained hosts that have grown in vitro are grafted to the central nerve system or peripheral nerves to take so as to allow the host cells to function as neurons, thereby treating intractable neuronal diseases associated with neurological functional disorder, such as Parkinson's disease, amyotrophic lateral sclerosis, Huntington's chorea, Alzheimer's disease, brain infarction, spinal cord injury, brain contusion or malignant tumor.

6 Claims, No Drawings

```
SEQUENCE LISTING

<160> NUMBER OF SEQ ID NOS: 4

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Synthetic

<400> SEQUENCE: 1
ctgaattcac catgccccgg agggcggag                                29

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence:Synthetic

<400> SEQUENCE: 2
gagaattctc aatctcccat ccgttgatg                                29

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:Synthetic
```

```
<400> SEQUENCE: 3
cgaggtgctc ttgggtcagc                                            20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 4
gaaagggcag actcggtggc                                            20
```

HOST CELLS OBTAINED BY INTRODUCING AND EXPRESSING VHL GENE IN CANCER CELLS OR EMBRYONIC STEM CELLS

This application is a divisional of Ser. No. 10/381,488, filed Mar. 26, 2003, now abandoned, which is a 371 U.S. national stage of International Application No. PCT/JP00/06668 filed Sep. 27, 2000.

TECHNICAL FIELD

The present invention relates to host cells that can function as neurons obtained by introduction and expression of von Hippel-Lindau gene (VHL gene) in cancer cells such as neuroblastoma cells, anaplastic oncocytes derived from the nerve system, or embryonic stem cells. Particularly, the present invention relates to the above host cells for treating patients with diseases associated with neurological functional disorder by grafting the host cells to the central nerve system or peripheral nerves so as to take, and allowing the host cells to function as neurons.

BACKGROUND ART

A neuron is a main element controlling the life activity of an individual higher organism. It had been thought that neurons of the central nerve system perform neither postnatal differentiation nor regeneration, but only deciduate from one minute to the next. However in the 1990s, neuronal stem cells which had not yet differentiated into neurons were found in a fetal brain, and further the presence of neuronal stem cells in an adult brain was also proved. Thus, the possibility of regeneration of the central nerve system has been suggested. Now, possible therapy using neuronal stem cells for intractable neuronal diseases, and therapy using embryonic stem cells (ES cells, also called as universal cells which can differentiate into any type of cells) are stepping into the limelight.

However, since human neuronal stem cells can only be collected from human fetal brain resulting from artificial termination of pregnancy, there are ethical issues to surmount. Further, securing the dose required to treat neurological diseases is difficult because the amount of such stem cells that can be collected is limited. Furthermore, there is another problem that only a portion of neuronal stem cells collected with considerable effort, differentiate into neurons and most of them differentiate into glial cells.

Regarding these problems, we have considered that VHL gene and VHL gene products may play a role from the developmental stage of neurons based on the fact that they are specifically expressed in neurons of the central nerve system. Accordingly, our studies on expression of VHL gene products in neuronal stem cells have revealed that VHL gene products are mainly expressed in the cytoplasm as neuronal stem cells differentiate into neurons. Further, introduction of VHL gene into neuronal stem cells using a herpes simplex virus vector resulted in promotion of differentiation into neurons. Hence, we have shown that VHL gene is a gene involved in induction of neuronal differentiation in neuronal stem cells (Kanno H: Cancer Res 2820-4, 2000). However, neuronal stem cells are known from the beginning to differentiate into either neurons or glial cells. Addition of basic fibroblast growth factor (bFGF) into a medium also results in a similar phenomenon. Therefore, whether or not VHL gene itself possesses an ability to induce direct differentiation into nerves remains unknown.

On the other hand, unlike neuronal stem cells, immortalized cancer cells or ES cells can be cultured in vitro infinitely. However, the mechanism of their differentiation is unknown and almost nothing is revealed about a possible application thereof to regenerative medicine. For example, engineering of which gene (and how differentiation occurs) can be applied to regenerative medicine remains unknown. Moreover, no one has succeeded in inducing differentiation into neurons by simply introducing a specific gene into immortalized cancer cells or ES cells for which it is very difficult to induce differentiation into neurons compared to neuronal stem cells. Among cancer cells, neuroblastoma cells (which are established from neuroblastoma, a kind of childhood cancer, developed from adrenal gland) are known to extend neuron-like projections when retinoic acid is added in the medium. However, neuroblastoma cells do not differentiate into true neurons having function to transmit electric signals. Known methods for differentiating cultured ES cells into neuronal stem cells and then to neurons include a method which adds retinoic acid into a medium (Fraichard A, et al.: J Cell Sci 108: 3181-8, 1995) and a method which adds basic fibroblast growth factor (bFGF) to cause differentiation to neurons at a relatively high rate (Okabe S, et al.: Mech Dev 59: 89-102, 1996). However, not all of the cells can differentiate into neurons by these methods and distinguishing between neuronal stem cells and neurons is required. Further, it is thought that these methods require 6 or more days to induce differentiation of ES cells into neurons.

In contrast to induction of differentiation into neurons, controlling differentiation is also an important technique. Regarding this technique, some cancer suppressor genes have been reported to have such a control function. Regarding control of neuronal differentiation using antisense of a gene which induces neuronal differentiation, we have reported that differentiation from neuronal stem cells into neurons is controlled by the antisense sequence (antisense) of VHL gene (Kanno H, et al.: Cancer Res 60: 2820-2824, 2000). Control of differentiation from cancer cells or ES cells has not been reported.

In the United States, clinical trials using fetal brain obtained by artificial termination of pregnancy for treating Parkinson's disease have been already conducted and a certain effect has been recognized. At the level of animal experiment, a trial, in which neuronal stem cells or ES cells are grafted to the brain or spinal cord, and the cells are allowed to differentiate into neurons, has been started to treat intractable neuronal diseases including not only Parkinson's disease, but also brain infarction, spinal cord injury and the like. Moreover, regeneration of peripheral nerve in vitro or in vivo in the form of bundles of nerve fibers has been attempted. However, since neurons do not principally divide and proliferate, it is difficult to form practical bundles of nerve. In nerve grafting to treat ruptured peripheral nerve, normally the autologous nerve of a lower limb is excised and grafted. However, production of artificial nerve for nerve grafting in place of autologous nerve has not been successful.

DISCLOSURE OF THE INVENTION

The purpose of the present invention is to provide host cells that can function as neurons obtainable by introduction and expression of VHL gene in cancer cells or embryonic stem cells. Another purpose of the present invention is to provide a method for obtaining neurons for treating patients with diseases associated with damaged neurological function from neuroblastoma cells, anaplastic oncocytes derived from the nerve system, or embryonic stem cells. Still another purpose of the present invention is to provide a method for inhibiting differentiation from cancer cells or ES cells into neurons by antisense techniques.

As a result of thorough studies to solve the above problems, we have completed the present invention by finding that introduction of a VHL gene into cancer cells, such as neuroblastoma cells and anaplastic oncocytes derived from the nerve system enables differentiation into neurons, and introduction of a VHL gene into embryonic stem cells enables differentiation into neurons via neuronal stem cells.

The present invention encompasses the following inventions.

(1) A host cell obtained by introducing and expressing von Hippel-Lindau gene in a cancer cell.

(2) The host cell of (1) in which the cancer cell is a neuroblastoma cell.

(3) The host cell of (1) in which the cancer cell is an anaplastic oncocyte derived from the nerve system.

(4) The host cell of (1) which has the following properties:
(a) expresses neuro-peptide Y and neurofilament as neuron specific proteins and secretes neuro-peptide Y extracellularly;
(b) extends neurite with varicosity typical of neurons and is capable of forming a neural circuit;
(c) has a membrane potential which is typical of neurons and is capable of transmitting electric signals; and
(d) is able to take when grafted to the central nerve system or peripheral nerves after in vitro culturing and growth.

(5) A host cell which is obtained by introducing and expressing von Hippel-Lindau gene in an embryonic stem cell.

(6) The host cell of (5) which has the following properties:
(a) expresses neuro-peptide Y, neurofilament, and microtubule associated protein 2(MAP2) as neuron specific proteins;
(b) is a mature neuron which can transmit electric signals as a nerve and can form a neural circuit;
(c) is capable of propagating action potential as a functional nerve and forming a neural circuit; and
(d) is able to take when grafted to the central nerve system or peripheral nerves after in vitro culturing and growth.

(7) The host cell of (1) or (5) for treating a patient with a disease associated with neurological functional disorder by getting a graft take of the cell into the central nerve system or peripheral nerve and allowing the cell to function as a neuron.

(8) The host cell of (7) in which the disease is Parkinson's disease, amyotrophic lateral sclerosis, Huntington's chorea, Alzheimer's disease, brain infarction, spinal cord injury, brain contusion or malignant tumor.

(9) A method for obtaining a neuron by introducing von Hippel-Lindau gene into a cancer cell and inducing neuronal differentiation.

(10) The method of (9) in which the cancer cell is a neuroblastoma cell.

(11) The method of (9) in which the cancer cell is an anaplastic oncocyte derived from the nerve system.

(12) A method for obtaining a neuron by introducing von Hippel-Lindau gene into an embryonic stem cell, and inducing neuronal differentiation via a neuronal stem cell.

(13) A method for inhibiting differentiation from a neuronal stem cell to a neuron comprising inhibiting expression of von Hippel-Lindau gene by introducing antisense RNA or antisense DNA into a cancer cell or an embryonic stem cell.

BEST MODE FOR CARRYING OUT THE INVENTION

The present invention will be described in detail as follows.

A VHL gene, which is the causative gene of von Hippel-Lindau disease, a hereditary disease causing brain tumor (hemangioblastoma) or renal cell carcinoma, is a kind of a tumor suppressor gene. This gene was isolated from human chromosome 3 by Dr. Zbar et al.'s group (U.S.A.) in 1993. It has been reported that the VHL gene and the protein are expressed in neurons. However, the function of this gene in the nerve system was unknown. We considered that the gene may be involved in the formation of the nerve system at fetal developmental stages and studied differentiation over time of neuronal stem cells isolated from a rat fetal brain. Thus, we have found that VHL proteins are expressed in neurons as neuronal stem cells differentiate into neurons.

The present invention is based on the following findings:

(a) introduction and expression of VHL gene in immortalized cells of human neuroblastoma, which is a type of childhood cancer and developed from neurons of the adrenal gland, can rapidly and directly induce differentiation into proliferative neurons which have true neurological function to transmit electric signals and can form neural circuits (network); and (b) introduction and expression of VHL gene in ES cells, which are called universal cells, that can differentiate into any type of cell constituting a higher organism individual, can induce differentiation from neuronal stem cells to neurons reliably and in a short period of time. Host cells obtained by introducing and expressing VHL gene into human neuroblastoma cells have the following properties:
(a) expresses neuron specified proteins and secretes part thereof;
(b) extend neurite with varicosity which is typical of neurons and are capable of forming neural circuits (neuronetwork);
(c) have a measurable membrane potential which is typical of neurons, and are capable of transmitting electric signals; and
(d) are able to take when grafted to the central nerve system or peripheral nerves after in vitro culturing and growth. Further, host cells obtained by introduction and expression of VHL gene into ES cells have the following properties:
(a) are mature neurons which can transmit electric signals as nerve and can form neural circuits (neuronetwork);
(b) are neurons that can proliferate and be cultured in large quantity in vitro and can be grafted to the central nerve system and peripheral nerves; and
(c) have potential to recover neurological functional disorder when grafted in vivo to take and function as neurons.

Based on the above result that VHL gene has the ability to induce neuronal differentiation in neuronal stem cells, we have postulated that VHL gene can induce neuronal differentiation also in other cells of the nerve system. We have obtained neuroblastoma, in which VHL genes are always strongly expressed, by introducing VHL gene using a plasmid expression vector with VHL gene incorporated therein, into immortalized cells of human neuroblastoma (a kind of childhood cancer) that has developed from the neurons of the adrenal gland. Then, we have examined the properties of the obtained cells. As a result, the morphology of the cell changed in a way typical of neurons, expression of genes and proteins found only in neurons was confirmed, and the miniature potential across the cell membrane found only in neurons was also confirmed. These results suggest that the neuroblastoma with VHL gene introduced therein changed into cells very similar to neurons. Therefore, we have found that diseases in which neurons are disrupted (Parkinson's disease, Alzheimer's disease, spinal cord injury, brain infarction and the like) can be treated by grafting the artificially generated cells or neurons that have differentiated from neuronal stem cells obtained by introducing VHL gene.

Further, neuro differentiation was inhibited by using antisense oligonucleotides which had been designed to be targeted for messenger RNA of VHL gene in order to control differentiation of neurons from neuronal stem cells. Furthermore, we have succeeded in differentiation (conversion) from neuronal stem cells to neurons by introducing VHL gene using a virus vector. These results show that VHL gene induces differentiation from neuronal stem cells to neurons (Kanno H, et al.: Cancer Research 60:2840-2824, 2000). No gene having such an ability has been reported so far.

We have introduced VHL gene into embryonic stem cells in a similar way, which are an origin for all cells, showing that most cells differentiated into neurons via neuronal stem cells. The neurons produced by the method can be applied to therapy for the above diseases with disrupted nerve (intractable neuronal diseases) by grafting the neurons.

VHLcDNA (g7-11) used as VHL gene to be introduced into host cells can be obtained by the following method. First, normal brain or renal tissue is homogenized with guanidine isothiocyanate-containing phenol or phenol/chloroform solution. Then the product is separated into an aqueous layer and an organic layer by high speed centrifugation, the aqueous layer is added to isopropanol to precipitate total RNA contained therein, and then the precipitate is collected. Next, cDNA is synthesized from mRNA in the presence of reverse transcriptase. The polymerase chain reaction (PCR) is performed to amplify a region of interest using a primer set of
5'-CTGAATTCACCATGCCCCGGAGGGCGGAG-3' (SEQ ID NO: 1) and 5'-GAGAATTCTCAATCTCCCATC-CGTTGATG-3' (SEQ ID NO: 2) in a thermal cycler. Then the product is purified and incorporated into a vector.

Examples of such a vector that can be used include animal virus vectors, for example, retrovirus or vaccinia virus. To insert the above VHL gene into a vector, for example, a method may be used which involves cleaving the purified DNA containing the above VHL gene with appropriate restriction enzymes, and inserting into the restriction enzyme site or multicloning site of an appropriate vector DNA to ligate to the vector.

The above VHL gene should be incorporated into a vector so that it can exert its function. In addition to a promoter and VHL gene, if necessary, a sequence containing a cis-element, such as an enhancer, a splicing signal consisting of a splicing donor site located on the 5' terminus of an intron and a splicing acceptor site located on the 3' terminus of an intron, poly (A) addition signal, selectable marker, ribosome binding sequence (SD sequence) and the like can be linked to the vector of the present invention. Further, examples of a selectable marker include a dihydrofolate reductase gene, ampicillin resistance gene, and neomycin resistance gene.

A SRα promoter, SV40 promoter, LTR promoter, CMV promoter or the like is used as a promoter. An early gene promoter of human cytomegalo virus and the like may also be used. Examples of a method for introducing a recombinant vector into an animal cell include electroporation, a calcium phosphate method, and a lipofection method.

Culturing of the transformant of the present invention is performed according to a method normally employed for culturing a host.

Culturing is normally performed by shake culture or culture with aeration-agitation under aerobic conditions at 37° C. Further, pH of a medium is adjusted using inorganic or organic acid, alkali solution or the like.

Examples of a medium used herein for culturing transformants include a generally employed RPMI 1640 medium, DMEM medium, or these media supplemented with fetal calf serum and the like.

Culturing is normally performed in the presence of 5% $CO_2$ at 37° C. for 1 to 30 days. If necessary, antibiotics, such as kanamycin, penicillin and the like may be added to a medium while culturing.

Specifically, the above VHL gene is incorporated into a plasmid expression vector (pcDNA3.1, Invitrogen; the vector contains a CMV promoter, a SV40 replication origin, a neomycin resistance gene, a ColE1, an ampicillin resistance gene and the like) having a neomycin resistance gene incorporated therein.

The plasmid expression vector pcDNA3.1 with VHL gene incorporated therein is introduced into neuroblastoma cells (SH-SY5Y) cultured in a DMEM or DMEM/F12 medium, which is prepared to have a neomycin (Genecitin, GIBCO BRL) concentration of 200 μg/mL and supplemented with 10% fetal calf serum, using a transfection reagent (Effectene™, transfection reagent (QIAGEN)). Only expressing clones are selected and allowed to proliferate. At this time, a cell used for introduction may be a neuroblastoma cell other than SH-SY5Y. Further, a vector used herein may be an expression vector other than a plasmid expression vector.

Before introduction of a VHL gene, cancer cells, such as neuroblastoma cells (SH-SY5Y) are cultured in a DMEM medium (containing 10% fetal calf serum), while adhering to the bottom of a petri dish 3003 (Falcon) under conditions of 5% $CO_2$ and 37° C. within a carbon dioxide culture apparatus. Sub-culturing is performed every 4 days at a 1:6 split ratio.

After introduction of VHL gene, neuroblastoma cells (SH-SY5Y) can be cultured in DMEM or DMEM/F12 medium, which is prepared to have a neomycin (Genecitin, GIBCO BRL) concentration of 200 μg/mL and supplemented with 10% fetal calf serum, while adhering to the bottom of a petri dish 3003 (Falcon) under conditions of 5% $CO_2$ and 37° C. within a Carbon dioxide culture apparatus. Sub-culturing of the cells is performed every 6 days at a 1:6 split ratio.

Before introduction of a VHL gene, ES cells are cultured according to Bain et al.'s method (Bain G, et al.: Developmental Biology 168: 342-357, 1995).

Expression of VHL proteins and neuron specific proteins in cancer cells (neuroblastoma cells, anaplastic oncocytes derived from the nerve system) and ES cells (host cells), with VHL gene introduced therein, is examined by the following method. NPY, NFH, and MAPs are examined as neuron specific proteins. This method is performed according to the method described in the paper by Kanno et al. (Kanno H, et al.: Cancer Res 60: 2820-2824, 2000) by a fluorescence immuno-staining method. Observation is made using confocal laser fluorescence microscopy. The VHL protein and neuron specific protein are expressed in the same cell at the same time.

Secretion of neuron specific proteins from cancer cells (neuroblastoma cells, anaplastic oncocytes derived from the nerve system) and ES cells (host cells) with VHL gene introduced therein was examined by ELISA method according to the method described in another paper by Kanno et al. (Kanno H, et al.: Cancer Gene Therapy 6(2): 147-154, 1999). Release of NPY from openings by extracellular potential stimulation with potassium ion and choline stimulation with carbachol is observed in host cells.

The morphologies of cancer cells (neuroblastoma cells, anaplastic oncocytes derived from the nerve system) and ES cells (host cells) with VHL gene introduced therein are observed using a phase contrast microscope. When the cells have differentiated into mature neurons, varicosity will be observed on the neurite.

Electroneurophysiological findings are examined by the following method. When cells are pricked with micro needle electrodes and intracellular potential is measured in patch clamp method, large sodium channel and potassium channel currents, such as those seen in neurons, are measured.

Cancer cells (neuroblastoma cells, anaplastic oncocytes derived from the nerve system) and ES cells (host cells) with VHL gene introduced therein are grafted by the following method. First, host cells are previously well washed with a serum-free medium, such as DMEM, and then prepared in physiological saline at a concentration of 100,000 cells or more/0.1 mL. When cells are grafted to a brain, 100,000 to 10,000,000 cells are grafted into a target site within the brain using a stereotaxic neurosurgical appliance, or using an injection device (Ommaya reservoir and the like) previously embedded in the brain. Alternatively, the cells are grafted by a method which injects from the lumbar part into medullary space with a spinal injection needle.

The present invention provides an oligonucleotide which targets for nucleic acids encoding VHL and can inhibit expression of VHL.

A preferred oligonucleotide of the present invention is a chimeric oligonucleotide. The chimeric oligonucleotide comprises at least one nucleotide and contains two or more chemically different regions. The oligonucleotides also comprise at least one modified nucleotide region which confers one or more advantageous properties (for example, increased nuclease resistance, and increased intake into a cell and increased binding affinity to RNA target) and a region which is a substrate for RNaseH cleavage. In one preferred embodiment, a chimeric oligonucleotide comprises at least one region which is modified to increase binding affinity with a target, and a region which normally functions as a substrate for RNAseH. The affinity of an oligonucleotide to nucleic acids encoding VHL is determined by measuring Tm of a pair of oligonucleotide/target, which is a temperature at which the oligonucleotide and the target dissociate from each other. A high Tm increases the affinity of an oligonucleotide to a target. In amore preferred embodiment, the region of an oligonucleotide which is modified to increase VHL mRNA binding affinity comprises 2'—O-alkyl or 2'-Fluoro-modified nucleotide and the like in which a sugar molecule at position 2' is modified. The above modified oligonucleotide has binding affinity for a target higher than that of 2'-deoxyoligonucleotide. The effect of such increased affinity increases inhibition of VHL gene expression by an antisense oligonucleotide. RNaseH is a cellular endonuclease which cleaves the RNA strand of a RNA:DNA duplex. Activation of this enzyme causes the RNA target to be cleaved and makes antisense inhibition more effective. In another preferred embodiment, chimeric oligonucleotides are also modified to enhance nuclease resistance. Since cells contain various exo- and endo-nucleases which decompose nucleic acids, introduction of many modified nucleotides and nucleosides into oligonucleotides make the oligonucleotides to be more resistant to nuclease digestion compared to natural oligonucleotides. Nuclease resistance is measured by incubating oligonucleotides together with cell extracts or isolated nuclease solution, and quantifying remaining original oligonucleotides by gel electrophoresis. A modified oligonucleotide has a longer life time than that of an unmodified oligonucleotide. A preferred oligonucleotide comprises at least one phosphorothioate modification. Modified oligonucleotides with enhanced binding affinity for target nucleic acids can increase nuclease resistance.

A preferred oligonucleotide of the present invention contains phosphorothioate, phosphotriester, methylphosphonate bonds and the like. The most preferred oligonucleotide contains phosphorothioate and $CH_2$—NH—O—$CH_2$ and the like. In another preferred embodiment, the phosphodiester main chain of an oligonucleotide, for example, protein-nucleic acid or peptide-nucleic acid (PNA) main chain, may be substituted with a polyamide main chain. Other preferred oligonucleotides may contain one of OH, SH, $SCH_3$, F. OCN, $OCH_3OCH_3$ groups and the like at position 2'.

The length of the antisense oligonucleotide of the present invention is preferably approximately 8 to 50 nucleotides. In the present invention, an oligomer which comprises 8 to 50 nucleotides and does not exist in nature may be included.

The antisense oligonucleotide of the present invention can by synthesized by a known solid phase synthesis method. A device for solid phase synthesis is, for example, marketed by Applied Biosystems. Another method for producing oligonucleotides using phosphorothioate and alkylating derivatives may be used.

A type of oligonucleotide which targets for part of VHL mRNA has been found to be especially useful in inhibiting VHL expression. Examples of such antisense oligonucleotides are those represented by the following SEQ ID NOS: 3 and 4.

```
5'-CGAGGTGCTCTTGGGTCAGC-3'    (SEQ ID NO: 3)

5'-GAAAGGGCAGACTCGGTGGC-3'    (SEQ ID NO: 4)
```

In the method of the present invention, tissues or cells are allowed to contact with antisense oligonucleotides. That is, in the present invention, tissues or cells are allowed to contact with one or more antisense oligonucleotides by adding antisense oligonucleotides in vitro or ex vivo to a cell suspension or a tissue sample; or administering antisense oligonucleotides to cells or tissues in an animal.

The present invention provides a method for inhibiting cells for the purpose of therapy. The antisense oligonucleotides of the present invention, together with pharmaceutically applicable carriers, are administered to a patient to be treated in doses and for time periods which vary depending on the properties of a certain disease, its severity and the overall conditions of the patient.

The pharmaceutical composition of the present invention is administered locally, orally or parenterally, for example by intravenous drip, intravenous, subcutaneous, intraperitoneal or intramuscular injection.

Examples of a pharmaceutical formulation for local administration include paste, lotion, cream, gel, drop, suppository, spray, solution and powder. Normal pharmaceutical carriers, such as aqueous, powdery or oil base, thickener and the like are used.

Examples of a composition for oral administration include a powdered drug or a granule, a suspension pharmaceutical, water, water insoluble powder, a capsule, and a tablet. A thickener, flavoring agent, diluent, emulsifier, dispersing agent, binder or the like may be used.

Examples of a formulation for parenteral administration include a buffer, a diluent and a sterile aqueous solution which may contain other appropriate additives.

In addition to the above pharmaceutical carriers, cationic fluid may be added to a pharmaceutical formulation to facilitate the intake of antisense oligonucleotides.

Dosage will vary depending on the severity of the conditions and the response of a patient to be treated. Treatment is continued for several days to several months until the therapy is achieved or the disease conditions are alleviated. The optimum dosage plan can be established by determining the optimum dosage, manner of administration and frequency of repetition based on in vivo cumulative dosage. The optimum dosage varies depending on relative efficacy of respective antisense oligonucleotides, and it can be generally calculated based on $EC_{50}$ from in vitro and in vivo animal experiments. For example, an applied dose at mg/kg can be easily calculated from the molecular weight of a compound and the effective dose, such as $IC_{50}$.

EXAMPLE

Now the present invention will be further described in detail by the following examples which are intended for explanation only, and are not intended to limit the technical scope of the invention.

Example 1

When cells for gene transfer were neuroblastoma cells SH-SY5Y, VHLcDNA (g7-11), which was used as a VHL gene to be introduced, was obtained by the following method. First, normal renal tissue obtained from hypernephroma surgery was homogenized with guanidine isothionate-containing phenol or phenol/chloroform solution, and then separated into an aqueous layer and an organic layer by high speed centrifugation. The aqueous layer was added to isopropanol to precipitate total RNA obtained therein and the precipitate was collected. After cDNA was synthesized from mRNA in the presence of reverse transcriptase, a region of interest was amplified by the polymerase chain reaction (PCR) method using a primer set of 5'-CTGAATTCACCATGCCCCG-GAGGGCGGAG-3' (SEQ ID NO:1) and 5'-GAGAATTCT-CAATCTCCCATCCGTTGATG-3' (SEQ ID NO: 2) and using a thermal cycler (MJ Research). Then the amplified product was purified using a DNA purification kit (Amicon), and then incorporated into a plasmid expression vector (pcDNA3.1, Invitrogen) containing a neomycin resistance gene incorporated therein.

The plasmid expression vector pcDNA3.1 with VHL gene incorporated therein was introduced into neuroblastoma cells (SH-SY5Y) being cultured in a DMEM (GIBCO BRL) medium, which had been prepared to have a neomycin (Genecitin, GIBCO BRL) concentration of 200 μg/mL and supplemented with 10% fetal calf serum, using a transfection reagent, Effectene (QIAGEN). Only expressing clones were selected and allowed to proliferate.

Before introduction of VHL gene, neuroblastoma cells (SH-SY5Y) were cultured in a DMEM medium containing 10% fetal calf serum, while adhering to the bottom of a petri dish 3003 (Falcon) under conditions of 5%: $CO_2$ and 37° C. within a carbon dioxide culture apparatus. Sub-culturing was performed every 4 days at a 1:6 split ratio.

After introduction of VHL gene, neuroblastoma cells (SH-SY5Y) were cultured in a DMEM medium which had been prepared to have a neomycin (Genecitin, GIBCO BRL) concentration of 200 μg/mL and supplemented with 10% fetal calf serum, while adhering to the bottom of a petri dish 3003 (Falcon) under conditions of 5% $CO_2$ and 37° C. within a Carbon dioxide culture apparatus. Sub-culturing of the cells was performed every 6 days at a 1:6 split ratio.

Expression of VHL proteins and neuron specific proteins in neuroblastoma cells SH-SY5Y (host cells) with VHL gene introduced therein was examined by the following method. NPY and NFH were examined as neuron specific proteins by a fluorescent immuno-staining method. This method was performed according to a paper by Kanno et al. (Kanno H, et al.: Cancer Res 60: 2820-2824, 2000). Observation was made using confocal laser fluorescence microscopy (Bio-Rad). The VHL protein and neuron specific protein were expressed in the same cell at the same time.

Secretion of neuron specific proteins from neuroblastoma cells (host cells) with VHL gene introduced therein was examined by ELISA method according to the method described in another paper by Kanno et al. (Kanno H, et al.: Cancer Gene Therapy 6(2): 147-154, 1999). Release of NPY from openings due to extracellular potential stimulation with potassium ion and choline stimulation with carbachol was observed in host cells.

The morphology of neuroblastoma cells SH-5YSY (host cells) with VHL gene introduced therein was observed using a phase contrast microscope. With cells which had differentiated into mature neurons, varicosity was observed on the neurite.

Electroneurophysiological findings were examined by the following method. The cells were pricked with micro needle electrodes and intracellular potential was measured by a patch clamp method. Large sodium channel and potassium channel currents, such as those seen in neurons, were measured.

Neuroblastoma cells SH-5YSY (host cells) with VHL gene introduced therein were grafted by the following method. That is, the host cells previously washed well with a medium, such as a serum-free DMEM, were prepared in physiological saline at a concentration of 100,000 cells or more/0.1 mL. Then, to graft into a brain, the 100,000 cells were injected to the striate body of the brain using a stereotaxic neurosurgical appliance.

Example 2

When cells for gene transfer were ES cells, VHLcDNA (g7-11) used as VHL gene to be introduced was prepared by the following method. First, a normal renal tissue obtained from hypernephroma surgery was homogenized with guanidine isothiocyanate-containing phenol or phenol/chloroform solution, and then separated into an aqueous layer and an organic layer by high speed centrifugation. The aqueous layer was added to isopropanol to precipitate total RNA contained therein and the precipitate was collected. After cDNA was synthesized from mRNA in the presence of reverse transcriptase, a region of interest was amplified by the polymerase chain reaction (PCR) method using a primer set of 5'-CTGAATTCACCATGCCCCGGAGGGCGGAG-3' (SEQ ID NO: 1) and 5'-GAGAATTCTCAATCTCCCATC-CGTTGATG-3' (SEQ ID NO: 2) and using a thermal cycler (MJ Research). Then the amplified product was purified using DNA purification kit (Amicon), and then incorporated into a plasmid expression vector (pcDNA3.1, Invitrogen) containing a neomycin resistance gene incorporated therein.

Before introduction of a VHL gene, ES cells were cultured according to Bain et al.'s method (Bain G, et al.: Developmental Biology 168: 342-357, 1995).

The plasmid expression vector pcDNA3.1 with VHL gene incorporated therein was added and introduced into a DMEM/F12 medium (GIBCO BRL), which had been prepared to have a neomycin (Genecitin, GIBCO BRL) concentration of 200 μg/mL and supplemented with 10% fetal calf serum, using a transfection reagent, Effectene (QIAGEN). Only expressing clones were selected and allowed to proliferate.

Expression of VHL proteins and neuron specific proteins in ES cells (host cells) with VHL gene introduced therein was examined. That is, MAPs were examined as neuron specific proteins by a fluorescent immuno-staining method. This method was performed according to a paper by Kanno et al. (Kanno H, et al.: Cancer Res 60: 2820-2824, 2000). Observation was made using confocal laser fluorescence microscopy (Bio-Rad). The VHL protein and neuron specific protein were expressed in the same cell at the same time.

Secretion of neuron specific proteins from ES cells (host cells) with VHL gene introduced therein was examined by ELISA method according to the method described in another paper by Kanno et al. (Kanno H, et al.: Cancer Gene Therapy 6(2): 147-154, 1999). Release of NPY from openings due to extracellular potential stimulation with potassium ion and choline stimulation with carbachol was observed in host cells.

The morphology of ES cells (host cells) with VHL gene introduced therein was observed using a phase contrast microscope. With cells that had differentiated into mature neurons, varicosity was observed on the neurite.

Electroneurophysiological findings were examined by the following method. The cells were pricked with micro needle electrodes and intracellular potential was measured by a patch clamp method, large sodium channel and potassium channel currents, such as those seen in neurons, were measured.

ES cells (host cells) with VHL gene introduced therein were grafted by the following method. That is, the host cells previously washed well with a medium, such as a serum-free DMEM, were prepared in physiological saline at a concentration of 100,000 cells or more/0.1 mL. Then, to graft to a spinal cord, 100,000 cells were directly injected into the dura of the spinal cord, from which dorsal vertebral arch had been excised, using an operating microscope (Zeiss).

INDUSTRIAL APPLICABILITY

Cancer cells, such as neuroblastoma cells, and anaplastic oncocytes derived from the nerve system, and ES cells, in which the VHL gene of the resent invention has been introduced and expressed, differentiate into neurons, so that neurons can be provided in large quantity for neuranagenesis. Further, the use of antisense techniques enables control of differentiation of cancer cells, such as neuroblastoma cells and anaplastic oncocytes derived from the nerve system, and ES cells. Furthermore, after in vitro culturing and growth of neuroblastoma cells, and anaplastic oncocytes derived from the nerve system, and ES cells, in which the VHL gene has been introduced and expressed, these cells are grafted to the central nerve system or peripheral nerves so as to take, and allowed to function as neurons, so as to enable treatment of intractable neuronal diseases (Parkinson's disease, amyotrophic lateral sclerosis, Huntington's chorea, Alzheimer's disease, brain infarction) and spinal cord injury, brain contusion or malignant tumor, those associated with neurological functional disorder. Moreover, the mechanism of the VHL gene shown by the present invention has opened a new way for developing a new therapeutic agent which induces neuronal differentiation.

SEQUENCE LISTING FREE TEXT

SEQ ID NOS: 1 to 4: synthesized DNA

The invention claimed is:

1. Artificially generated cells obtained by introducing and expressing a human von Hippel-Lindau gene into a human embryonic stem cell, wherein said artificially generated cells have the following properties:
   (1) express neuro-peptide Y, neurofilament, and microtubule associated protein 2(MAP2) as neuron specific proteins;
   (2) are mature neurons which can transmit electric signals as nerve, and can form neural circuits; and
   (3) are capable of propagating action potential as functional nerves.

2. The artificially generated cells according to claim 1, wherein the human von Hippel-Lindau gene is cDNA synthesized from mRNA obtained from human normal tissue in the presence of reverse transcriptase and a primer set.

3. The artificially generated cells according to claim 2, wherein the primer set comprises:

5'-CTGAATTCACCATGCCCCGGAGGGCGGAG-3', (SEQ ID NO: 1)
and
5'-GAGAATTCTCAATCTCCCATCCGTTGATG-3'. (SEQ ID NO: 2)

4. The artificially generated cells according to claim 3, wherein the cDNA is inserted into an expression vector for the expression of foreign mammalian genes.

5. The artificially generated cells according to claim 4, wherein the vector is a plasmid expression vector.

6. The artificially generated cells according to claim 2, wherein the human normal tissue is brain or renal tissue.

* * * * *

UNITED STATES PATENT AND TRADEMARK OFFICE
CERTIFICATE OF CORRECTION

PATENT NO. : 7,601,344 B2  
APPLICATION NO. : 11/640905  
DATED : October 13, 2009  
INVENTOR(S) : Hiroshi Kanno Page 1 of 1

It is certified that error appears in the above-identified patent and that said Letters Patent is hereby corrected as shown below:

On the Title page, item [73] the Assignee's name should read:

"Toagosei Co., Ltd., Tokyo (JP)" rather than "Cell Free Sciences Co., LTD., Tokyo (JP)".

Signed and Sealed this  
Twenty-seventh Day of August, 2013

Teresa Stanek Rea  
*Acting Director of the United States Patent and Trademark Office*